(12) United States Patent
Windmiller et al.

(10) Patent No.: US 11,045,142 B1
(45) Date of Patent: Jun. 29, 2021

(54) HETEROGENEOUS INTEGRATION OF SILICON-FABRICATED SOLID MICRONEEDLE SENSORS AND CMOS CIRCUITRY

(71) Applicant: Biolinq, Inc., San Diego, CA (US)

(72) Inventors: Joshua Windmiller, Del Mar, CA (US); Jared Rylan Tangney, Encinitas, CA (US)

(73) Assignee: Biolinq, Inc., San Diego, CA (US)

(*) Notice: Subject to any disclaimer, the term of this patent is extended or adjusted under 35 U.S.C. 154(b) by 222 days.

(21) Appl. No.: 15/961,793

(22) Filed: Apr. 24, 2018

Related U.S. Application Data

(60) Provisional application No. 62/492,142, filed on Apr. 29, 2017.

(51) Int. Cl.
*A61B 5/00* (2006.01)
*A61M 37/00* (2006.01)

(52) U.S. Cl.
CPC ............ *A61B 5/685* (2013.01); *A61B 5/0048* (2013.01); *A61M 37/0015* (2013.01); *A61M 2037/0046* (2013.01)

(58) Field of Classification Search
CPC ...... A61M 37/0015; A61M 2037/0046; A61B 5/685; A61B 5/0048
See application file for complete search history.

(56) References Cited

U.S. PATENT DOCUMENTS

| | | |
|---|---|---|
| 4,305,401 A | 12/1981 | Reissmueller et al. |
| 4,323,996 A | 4/1982 | Ganter |
| 4,407,295 A | 10/1983 | Steuer et al. |
| 5,131,390 A | 7/1992 | Sakaguchi et al. |
| 5,279,543 A | 1/1994 | Glikfeld et al. |
| 5,286,364 A | 2/1994 | Yacynych et al. |
| 5,540,828 A | 7/1996 | Yacynych |
| 5,730,714 A | 3/1998 | Guy et al. |
| 5,766,132 A | 6/1998 | Yasukawa et al. |
| 6,036,055 A | 3/2000 | Mogadam et al. |
| 6,139,718 A | 10/2000 | Kurnik et al. |
| 6,269,053 B1 | 7/2001 | Kawata et al. |
| 6,284,126 B1 | 9/2001 | Kurnik et al. |

(Continued)

FOREIGN PATENT DOCUMENTS

| | | |
|---|---|---|
| WO | WO2009034313 | 3/2009 |
| WO | WO2009064164 | 5/2009 |

(Continued)

*Primary Examiner* — Eric J Messersmith
(74) *Attorney, Agent, or Firm* — Clause Eight; Michael Catania

(57) ABSTRACT

A skin-adorned physiological or biochemical sensing device is disclosed herein. The device preferably comprises a first substrate and a second substrate. The first substrate comprises an array of solid microneedles designed to penetrate a biological interface to access a physiological fluid or tissue. Each microneedle is capable of electrical interface with the physiological fluid or tissue. The second substrate comprises integrated circuitry designed to transduce at least one signal produced by an electrophysiological or electrochemical reaction. A sensing device is formed that is capable of interpreting the signal arising from the electrophysiological or electrochemical reaction to ascertain the level of some physiological or biochemical entity.

19 Claims, 4 Drawing Sheets

(56) References Cited

U.S. PATENT DOCUMENTS

| | | |
|---|---|---|
| 6,413,396 B1 | 7/2002 | Yang et al. |
| 6,471,903 B2 | 10/2002 | Sherman et al. |
| 6,603,987 B2 | 8/2003 | Whitson |
| 6,814,845 B2 | 11/2004 | Wilson et al. |
| 6,862,466 B2 | 3/2005 | Ackerman |
| 6,908,453 B2 | 6/2005 | Fleming et al. |
| 7,097,776 B2 | 8/2006 | Raju |
| 7,132,054 B1 | 11/2006 | Kravitz et al. |
| 7,262,068 B2 | 8/2007 | Roy et al. |
| 7,343,188 B2 | 3/2008 | Sohrab |
| 7,344,499 B1 | 3/2008 | Prausnitz et al. |
| 7,429,333 B2 | 9/2008 | Chiou et al. |
| 7,456,112 B2 | 11/2008 | Lee |
| 7,493,232 B1 | 2/2009 | Surina |
| 8,022,292 B2 | 9/2011 | Arianpour et al. |
| 8,088,321 B2 | 1/2012 | Ferguson et al. |
| 8,574,165 B2 | 11/2013 | Marsh |
| 8,798,799 B2 | 8/2014 | Deo et al. |
| 9,551,698 B2 | 1/2017 | Huys et al. |
| 2003/0225360 A1 | 12/2003 | Eppstein et al. |
| 2004/0082875 A1* | 4/2004 | Donoghue ............ A61B 5/076 600/544 |
| 2006/0015061 A1 | 1/2006 | Kuo et al. |
| 2006/0173259 A1* | 8/2006 | Flaherty ............ A61B 5/0031 600/331 |
| 2007/0170054 A2 | 7/2007 | Wilsey |
| 2007/0213044 A1 | 9/2007 | Steingart et al. |
| 2009/0088652 A1 | 4/2009 | Tremblay |
| 2009/0143761 A1 | 6/2009 | Cantor et al. |
| 2009/0259118 A1 | 10/2009 | Feldman et al. |
| 2010/0286803 A1 | 11/2010 | Tillotson |
| 2012/0323097 A9 | 12/2012 | Chowdhury |
| 2013/0065257 A1 | 3/2013 | Wang et al. |
| 2013/0144131 A1 | 6/2013 | Wang et al. |
| 2014/0259652 A1 | 9/2014 | Pushpala |
| 2014/0275897 A1 | 9/2014 | Pushpala |
| 2014/0336487 A1 | 11/2014 | Wang et al. |
| 2015/0126834 A1* | 5/2015 | Wang ............... B32B 38/145 600/345 |
| 2018/0279929 A1* | 10/2018 | Huang ............ A61B 5/150984 |

FOREIGN PATENT DOCUMENTS

| | | |
|---|---|---|
| WO | WO2010120364 | 10/2010 |
| WO | WO2012020332 | 2/2012 |
| WO | WO2013058879 | 4/2013 |

\* cited by examiner

HETEROGENEOUS INTEGRATION OF SILICON-FABRICATED SOLID MICRONEEDLE SENSORS AND CMOS CIRCUITRY

CROSS REFERENCE TO RELATED APPLICATION

The Present application claims priority to U.S. Provisional Patent Application No. 62/492,142, filed on Apr. 29, 2017, which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to sensors.

Description of the Related Art

The integration of silicon-fabricated microneedles with conventional silicon complementary metal-oxide semiconductor ("CMOS") circuitry is of utmost importance in perpetuating the miniaturization efforts of body-worn medical devices. Despite the current state of semiconductor miniaturization and packaging, the creation of a heterogeneous system comprised of microneedle-based sensors and the CMOS circuitry required to transduce the signals generated by such devices has posed a formidable challenge to those aiming to create low-profile, highly-integrated body-worn sensors for the quantification of physiological or biochemical signals. Indeed, leveraging state-of-the-art semiconductor processing and packaging methods in conjunction with CMOS-based circuitry and recent developments in minimally-invasive silicon-based microneedle devices for physiological and biochemical sensing would enable the construction of a self-contained sensing system in a single package.

U.S. Pat. No. 8,506,529 for a Method and structure of monolithetically integrated microneedle biochip discloses a method and device using CMOS and MEMS fabrication techniques for making an integrated microneedle device with integrated circuits. Merely by way of example, the technology can be applied to bio and chemical sensing, and other bioMEMS applications. In some embodiments, the integrated circuits are completed using standard IC processes. For example, an array of microneedles are fabricated on top of the IC substrate followed by formation of micro fluidic channels in the substrate. On-chip integrated circuits enable real-time sensing and intelligent drug delivery.

U.S. Pat. No. 5,953,306 for a Micro needle probe apparatus having probes cantilevered over respective electronic circuits, moving medium memory device including same and method of making same discloses micro needle probe apparatus that includes a probe and its associated electronic circuit. The electronic circuit is formed in a substrate and includes at least one metal interconnection layer. The probe is cantilevered over the electronic circuit and is composed of a metal probe arm, a support post that anchors one end of the probe arm to the substrate, and a micro needle mounted adjacent the moveable end of the probe arm. The probe apparatus may be used as the read/write mechanism of the moving-medium type memory device.

U.S. Pat. No. 8,452,369 for a CMOS compatible microneedle structures discloses an electronic device for sensing and/or actuating, the electronic device comprising at least one microneedle (10) on a substrate (1), each of the microneedles (10) comprising at least one channel (7, 8) surrounded by an insulating layer (6).

Prior art solutions have been concerned with the integration of silicon-based microneedle arrays and CMOS circuitry as discrete devices populating a printed circuit board; in certain circumstances, these metallic wires are coated with a layer of metal salt, such as a silver wire functionalized on the surface with a layer of silver chloride. Such integration fails to minimize device footprint, especially in x-y dimensions, since device area constitutes the summation of the area of any discrete CMOS circuitry, microneedle sensor(s), and area devoted to interconnect between these two entities on said printed circuit board. Under such a design philosophy, efforts have largely been devoted to ultra-large scale integration of CMOS circuitry and the creation of CMOS systems-on-a-chip to minimize the number of discrete CMOS devices populating a sensing system. Likewise, recent efforts have been directed at reducing the number of components required to realize microneedle-mediated sensing via the integration of electrophysiological and electrochemical sensors on self-contained solid microneedle devices, thereby obviating the need for separate hollow microneedle-based lumens for physiological fluid extraction and an adjoining chamber for which the chemical reaction and/or electrochemical detection are intended to occur. The heterogeneous integration of CMOS- and microneedle-based capabilities into a single package would facilitate a novel means to the construction of self-contained sensor-transducer devices that require substantially less footprint than conventional discrete constituents that comprise current body-worn sensing systems can provide.

BRIEF SUMMARY OF THE INVENTION

The technology described herein relates to methods of integration and packaging of heterogenous semiconductor substrates.

One aspect of the present invention is a skin-adorned physiological or biochemical sensing system. The system comprises a first substrate and a second substrate. The first substrate features an anterior and a posterior surface. The first substrate comprises an array of solid microneedles on the anterior surface designed to penetrate a biological interface to access a physiological fluid or tissue. Each microneedle contains an addressable metal electrode located on the surface of the microneedle which is in electrical communication with a metal surface located on the posterior surface of the first substrate by means of a conductive conduit, to form a sensor component capable of electrical interface with the physiological fluid or tissue. The second substrate has an anterior and a posterior surface. The second substrate comprises integrated circuitry on the anterior surface designed to transduce at least one signal produced by an electrophysiological or electrochemical reaction occurring at the metal electrode, to form a transducer component. The posterior surface of the first substrate is stacked to the anterior surface of the second substrate. The first substrate is bonded to the second substrate to create an electrical interconnect between the first substrate and the second substrate. A sensing system is formed that is capable of interpreting the signal arising from the electrophysiological or electrochemical reaction to ascertain the level of some physiological or biochemical entity.

Yet another aspect of the present invention is a method for the heterogeneous and monolithic integration of a semiconductor-based solid microneedles sensor and a semiconductor-based CMOS circuitry transducer. The method includes bonding a plurality of pads located on the posterior surface of sensor to a plurality of pads on either the anterior or posterior surface of a transducer to facilitate electrical communication between a sensor and the transducer. The sensor comprises a plurality of solid microneedles on the anterior surface of a substrate, each of the plurality of microneedles comprising an addressable sensing electrode. The transducer comprises a potentiostat, an analog front end, an amplifier, a filter, an analog-to-digital converter, microcontroller, and a wireless radio; Each of the plurality of sensing electrodes is accessible on a posterior surface of the substrate by means of a plurality of vertically-oriented conducting channels, wherein at a location on the posterior surface in which each of plurality of vertically-oriented conducting channels exit from the substrate. A plurality of conductive pads are positioned to facilitate bonding to the surface of a second substrate.

Yet another aspect of the present invention is a method for the heterogeneous and monolithic integration of a semiconductor-based solid microneedles sensor and a semiconductor-based CMOS circuitry transducer. The method includes mating a first substrate to a second substrate such that a posterior surface of the first substrate is bonded to an anterior surface of the second substrate. The first substrate contains a transducer and the second substrate containing a sensor. The sensor comprises a plurality of solid microneedles on the anterior surface of a substrate. Each of the plurality of microneedles comprises an addressable sensing electrode. The transducer comprises a potentiostat, an analog front end, an amplifier, a filter, an analog-to-digital converter, microcontroller, and a wireless radio. Each of the plurality of sensing electrodes is accessible on a posterior surface of the substrate by means of a plurality of vertically-oriented conducting channels, wherein at a location on the posterior surface in which each of plurality of vertically-oriented conducting channels exit from the substrate. A plurality of conductive pads are positioned to facilitate bonding to the surface of a second substrate.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
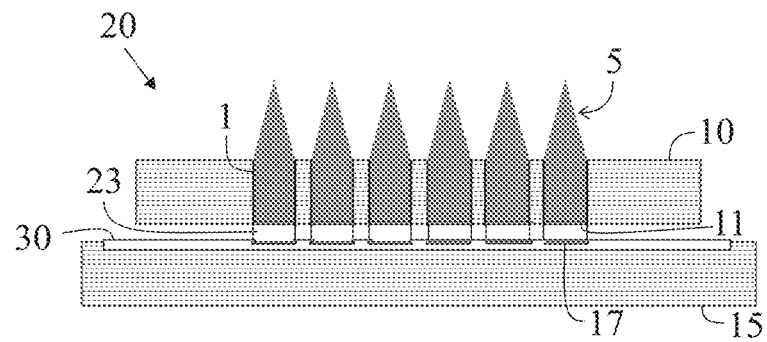
FIG. 1 is a diagrammatic representation of a die stack with CMOS circuitry on anterior surface of a second die.

To facilitate increased patient compliance and improve the treatment of acute or chronic disease, body-adorned medical devices such as non-invasive sensor patches as well as minimally-invasive subcutaneously- and intracutaneously-implanted sensors have substantially expanded in use over the past decade. Much of this proliferation has been a result of advancements in electrochemical sensor technology, which enables the quantification of circulating analytes in physiological fluids (blood, interstitial fluid, etc.) in miniaturized and compact platforms. These platforms, which integrate the sensor and transducer constituents into a single device, have been applied to such embodiments as continuous glucose monitoring. Although the current state-of-the-art has resulted in the widespread utilization of body-worn devices in the healthcare domain, the realization of truly low-profile and potentially skin-conformal skin-adorned or skin-adhered medical devices remains elusive as current limitations with electronic device packaging often entails the mounting and interconnect, in a 2-dimensional fashion, of discrete components populating a printed circuit board.

The present invention is a method for the three-dimensional ("3D") packaging and interconnection of heterogeneous, semiconductor-based systems for body-worn health and wellness devices, such as MEMS-fabricated microneedle arrays and CMOS-based transducers. One aspect of the present invention is a novel method of die attaching via stacking and interconnection of CMOS- and MEMS-based dies as a means to achieve 2.5D or 3D integration. Another aspect of the present invention is a method of fabricating CMOS and MEMS systems on geographically distinct regions of a shared surface of substrate whereby said systems are interconnected to one another by means of conductive traces or through-silicon vias. Another aspect of the present invention is a method of fabricating CMOS and MEMS on opposing surfaces of a substrate whereby interconnect between the two systems is facilitated by through-silicon vias. The ability to perform MEMS-to- CMOS packaging via stacked wire-bonding, reflow soldering of solder balls, or stud-bumping in conjunction with silicon or epoxy interposers enables the construction of vertically-integrated 2.5- or 3-dimensional self-contained sensing systems. Likewise, co-substrate integration of microneedles and CMOS circuitry represents another compelling solution enabled by through-silicon vias (TSVs), flip-chip bonding techniques, or a combination of these capabilities.

The monolithic integration of CMOS-based circuitry and microneedle-based transducers solves several noteworthy challenges confronting those developing technologies in the medical devices and wearable sensors domains. The present invention represents a novel approach to facilitating the synthesis of a heterogeneous, self-contained sensor-transducer system that addresses the shortcomings of the prior art while remaining amenable to highly scalable manufacturing processes.

These prior art shortcomings include the following:

(1) The necessity of interconnect of distinct microneedle-based sensors and CMOS-based transducers, as required for the readout of said microneedles, by means of integration as discrete packaged and mounted/bonded devices populating a printed circuit board: Limitation: A printed circuit board containing discrete microneedle and CMOS systems cannot be easily miniaturized beyond the xy-dimensions associated with said systems as well as the interconnects between the two, thereby placing a technological barrier to the realization of miniaturized skin-worn sensor devices. Moreover, routing electrical connections between two or more such discrete systems on a printed circuit board imposes added constraints of complexity and cost. Mitigation: The utilization of advanced semiconductor processing and packaging techniques facilitates the creation of 2.5- or 3-dimensional, self-contained microneedle-CMOS sensor-transducer systems or heterogeneously integrated microneedle-CMOS architectures sharing a common substrate.

(2) The interconnect of discrete microneedle-based sensors and CMOS-based transducers using conventional PCB traces: Limitation: Interconnect of distinct microneedle and CMOS systems on a printed circuit board is not amenable to maintaining signal fidelity, especially when such signals are analog in nature and reside in the nanoampere/microvolt (or lower) range. Mitigation: As the spatial extent of the interconnect between two electronic systems is directly proportional to noise ingress, the co-location of microneedle and CMOS systems on a shared substrate or the interconnect of said systems by means of solder balls/wire bonds serves to minimize the distance over which said systems interact and hence the noise imparted in the combined system. By reducing interconnect length between the microneedle sensor and CMOS transducer, the chief source of electronic noise and signal degradation is thus minimized.

(3) Inability to scale heterogeneous microneedle- and CMOS-based systems to dimensions enabling unobtrusive, conformal, and flexible skin-adorned medical patches: Limitation: Owing to their disparate manufacturing and packaging requirements, silicon micro-fabricated microneedles and CMOS circuitry have conventionally been packaged as mutually-exclusive, discrete entities populating a printed circuit board. Indeed, heterogeneous integration in a single package or on a single substrate presents difficulty owing to incompatibilities in manufacturing processes and packaging requirements. Mitigation: Employing a monolithic approach to microneedle and CMOS integration, either by means of co-locating the said constituents on the same substrate, or packaging the components as a single stacked entity, heralds the realization of highly miniaturized, self-contained sensing systems capable of direct integration into skin-adorned medical patches characterized by low footprint.

The technology disclosed herein specifies methods to achieve the heterogeneous and monolithic integration of semiconductor-based solid microneedles sensor and the semiconductor-based CMOS circuitry transducer required to interpret readings from the sensor. The sensor preferably contains one or a plurality of solid microneedles on an anterior surface of a substrate, each containing an addressable sensing electrode. The sensor is preferably designed to penetrate a biological interface to access a physiological fluid or tissue. The transducer preferably contains one or a plurality of integrated circuits using complementary metal oxide semiconductor (CMOS) technology. The transducer is preferably designed to control the sensor by applying a specific signal or stimulus to the sensor as well as interpreting the resulting electrical response of the sensor to the signal or stimulus. The transducer preferably includes at least one of the following components: a potentiostat, an analog front end, an amplifier, a filter, an analog-to-digital converter, microcontroller, and a wireless radio. Three approaches may be leveraged to achieve this aim of heterogeneous integration of the sensor and the transducer.

The stacked substrate 10: The sensing electrodes are accessible on the opposing (posterior) surface of the substrate by means of vertically-oriented conducting channels known as through-substrate vias (TSVs), and as described in more detail in Windmiller, et al., U.S. patent application Ser. No. 15/913,709, filed on Mar. 6, 2018, for Methods For Achieving An Isolated Electrical Interface Between An Anterior Surface Of A Microneedle Structure And A Posterior Surface Of A Support Structure is hereby incorporated by reference in its entirety. At a location on a posterior surface in which the TSVs exit from the substrate, conductive pads are found to facilitate bonding to the surface of a second substrate. The conductive pads are preferably located on the posterior surface of the sensor, and are bonded to conductive pads on either the anterior or posterior surface of the transducer to facilitate an electrical communication between the sensor and the transducer. Bonding is achieved by at least one of: stud bumps, solder balls, direct bonding, surface activated bonding, plasma activated bonding, fusion bonding, metal layer bonding, anodic bonding, eutectic bonding, glass frit bonding, insulating layer bonding, adhesive bonding, thermocompression bonding, reactive bonding, transient liquid phase diffusion bonding, physical bonding, and chemical bonding. Optionally, the sensor and the transducer may be wire-bonded to achieve electrical interface between the two systems. Optionally, the transducer (following mating with the sensor) may be mated, in a similar fashion as above, to another CMOS-containing substrate. Optionally, the transducer (following mating with the sensor) may be wire-bonded or stud-bumped and soldered to a printed circuit board to enable electrical communication with discrete electrical or electronic devices such as, but not limited to, batteries, antennas, resistors, capacitors, inductors, diodes, transistors, and discrete semiconductor components.

The Co-Substrate Integration: The sensing electrodes are accessible on the opposing (posterior) surface of the substrate by means of vertically-oriented conducting channels known as through-substrate vias (TSVs). At a location on the posterior surface in which the TSVs exit from the substrate, conductive traces are found to route signals generated by the sensor to the transducer to facilitate an electrical communication between the sensor located on the anterior surface of substrate and the transducer located on the posterior surface of substrate. Optionally, the substrate (hereinafter referred to as the first substrate) may be mated to another CMOS-containing substrate (second substrate) such that the posterior surface of the first substrate (containing the transducer) is bonded to the anterior surface of the second substrate by means of at least one of: stud bumps, solder balls, direct bonding, surface activated bonding, plasma activated bonding, fusion bonding, metal layer bonding, anodic bonding, eutectic bonding, glass frit bonding, insulating layer bonding, adhesive bonding, thermocompression bonding, reactive bonding, transient liquid phase diffusion bonding, physical bonding, and chemical bonding. Optionally, the first substrate or the second substrate (if present) may be wire-bonded or stud-bumped and soldered to a printed circuit board to enable electrical communication with discrete electrical or electronic devices such as, but not limited to, batteries, antennas, resistors, capacitors, inductors, diodes, transistors, and discrete semiconductor components.

The Co-Planar Integration: The sensing electrodes are accessible on the same (anterior) surface of the substrate by means of horizontally-oriented conducting traces. The conductive traces route electrical signals generated by sensor to the transducer to facilitate an electrical communication between the sensor and the transducer, both co-located on spatially distinct regions on the anterior surface of the substrate. Optionally, the substrate (hereinafter referred to as the first substrate) may be mated to another CMOS-containing silicon die (second substrate) such that the posterior surface of the first substrate is bonded to the anterior surface of the second substrate by means of at least one of: stud bumps, solder balls, direct bonding, surface activated bonding, plasma activated bonding, fusion bonding, metal layer bonding, anodic bonding, eutectic bonding, glass frit bonding, insulating layer bonding, adhesive bonding, thermocompression bonding, reactive bonding, transient liquid phase diffusion bonding, physical bonding, and chemical bonding. Optionally, the first substrate or the second substrate may be wire-bonded or stud-bumped and soldered to a printed circuit board to enable electrical communication with discrete electrical or electronic devices such as, but not limited to, batteries, antennas, resistors, capacitors, inductors, diodes, transistors, and discrete semiconductor components.

Under each of the above scenarios, the substrate may comprise a semiconductor wafer or die selected from one of the Group IV elements (i.e. Silicon, Germanium), the Group VI elements (i.e. Selenium, Tellurium), composites comprising II-VI elements (i.e. Cadmium Sulfide, Zinc Oxide), and composites comprising III-V elements (i.e. Gallium Arsenide, Indium Phosphide); the TSV may comprise the doped or intrinsically conducting species of the above materials as well as a metal.

The microneedle sensor 5 breaches a biological interface to access a physiological fluid or tissue. The microneedle sensor 5 contains one or a plurality of solid microneedles on the anterior surface of a silicon substrate 10, each of the microneedle constituents contain an addressable sensing electrode in physical contact with the physiological fluid or tissue. In addition, the sensing electrode(s) are in direct electrical communication either with another region on the anterior surface of the silicon substrate (by means of metallic traces/conduits) or on the posterior surface of the substrate (by means of through-silicon vias 1). The microneedle sensor 5 is designed to stimulate, sustain, and provide a means to read out some electrophysiological or electrochemical signal or reaction at the electrode surface.

The CMOS transducer 30 converts some variations in electrophysiological or electrochemical quantities arising at the interface of the microneedle sensor 5 and the biological interface into an electrical signal or vice versa. The CMOS transducer 30 transduces the signal(s) produced by the microneedle sensor 5 to information capable of being interpreted to ascertain the level of some physiological or biochemical entity. The CMOS transducer 30 contains complementary metal oxide semiconductor circuitry, patterned on a silicon substrate, to implement at least one of the following functionalities: a potentiostat, an analog front end, an amplifier, a filter, an analog-to-digital converter, microcontroller, and a wireless radio. Optionally the CMOS transducer 30 can control the microneedle sensor 5 by applying a certain potential, current, or frequency-modulated signal while simultaneously quantifying the electrical response of the microneedle sensor 5. Optionally the CMOS transducer 30 can perform processing on the signal to mitigate noise and can feature a wireless capability to relay said raw or processed signal to another device. Optionally the CMOS transducer 30 can interface with a display to present the user with sensor readings.

The semiconductor substrates 10 provide a mechanical support for the implementation of sensor and transducer constituents. The semiconductor substrates 10 are comprised of a semiconductor wafer or die selected from one of the Group IV elements (i.e. Silicon, Germanium), the Group VI elements (i.e. Selenium, Tellurium), composites comprising II-VI elements (i.e. Cadmium Sulfide, Zinc Oxide), and composites comprising III-V elements (i.e. Gallium Arsenide, Indium Phosphide).

Through-substrate via 1 facilitate an electrical interconnect between anterior and posterior surfaces of a semiconductor substrate 10. The through-substrate vias 1 are comprised of a doped or intrinsically conducting species of the Group IV, Group VI semiconductor elements or binary semiconductor compounds comprising the II-VI and III-V elements. Optionally the through-substrate vias 1 may be comprised of a metal or metal alloy. In the case that the substrate 10 is comprised of silicon, this is also referred to as a through-silicon via 1.

Stud bumps/solder balls/epoxy 23 facilitate an electrical interconnect between two disparate substrates (silicon 10, PCB 35, or combination of the two).

Bond wire 50 facilitates an electrical interconnect between two disparate substrates (silicon 10, PCB 35, or combination of the two). The bond wire 50 is preferably comprised of a metal or metal alloy.

Figure 1A:
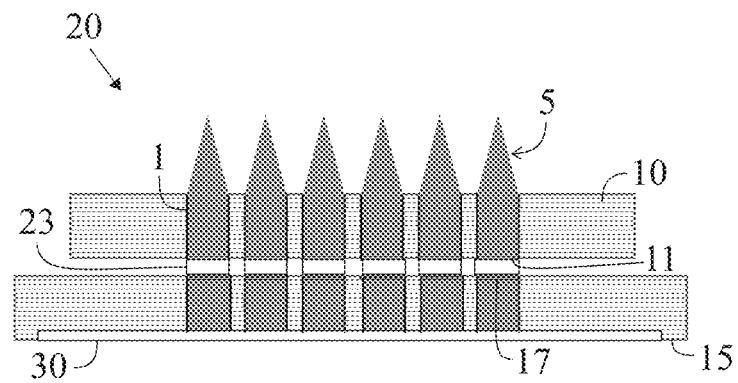
FIG. 1A is a diagrammatic representation of a die stack with CMOS circuitry on posterior surface of a second die.
Figure 1B:
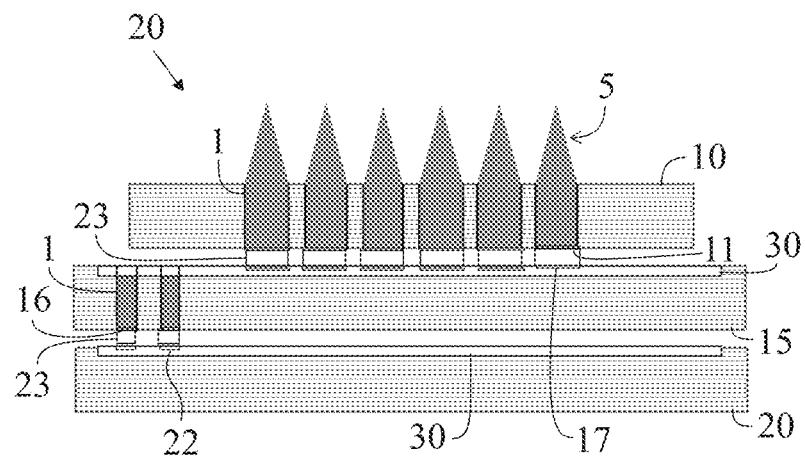
FIG. 1B is a diagrammatic representation of a die stack with CMOS circuitry on anterior surface of a second die and a third die.
Figure 1C:
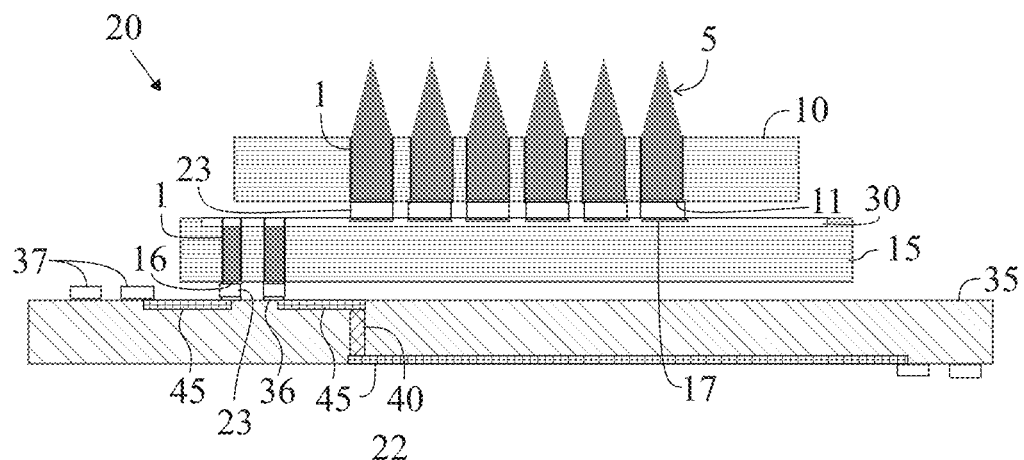
FIG. 1C is a diagrammatic representation of a die stack mounted on a printed circuit board containing assorted electrical circuit components, with CMOS circuitry on anterior surface of a second die.
Figure 1D:
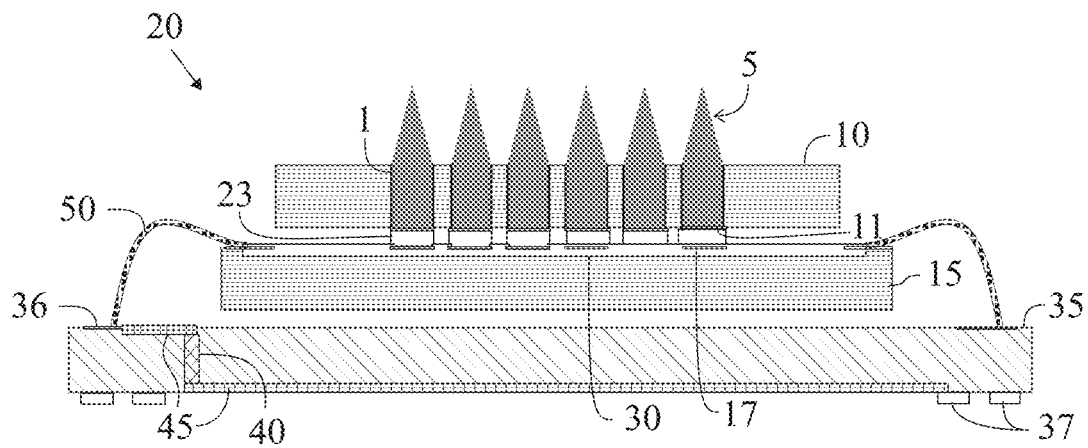
FIG. 1D is a diagrammatic representation of a die stack mounted on a printed circuit board containing assorted electrical circuit components, with CMOS circuitry on anterior surface of a second die.
Figure 1E:
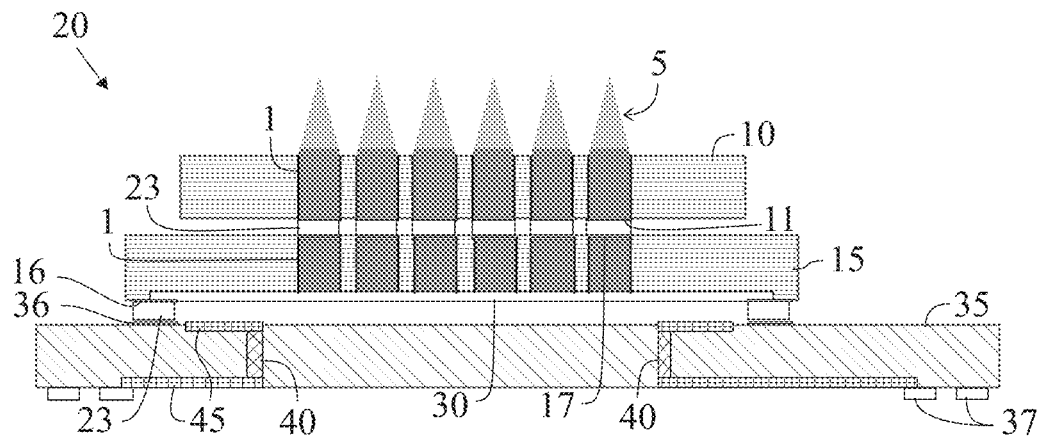
FIG. 1E is a diagrammatic representation of a die stack mounted on a printed circuit board containing assorted electrical circuit components, with CMOS circuitry on posterior surface of a second die.

FIGS. 1-1E illustrate diagrammatic representations of various die-stacking devices 20 that achieve heterogeneous integration of silicon-fabricated solid microneedle sensors and CMOS circuitry. FIG. 1 illustrates a skin-adorned physiological or biochemical sensing device 20 with a first die stack 10 with a CMOS circuitry 30 on an anterior surface of a second die 15. Each of the microneedles 5 is on a posterior pad 11 with stud bumps/sold balls/conductive epoxy 23 between the posterior pads 11 and anterior pads 17. FIG. 1A illustrates a first die stack 10 with CMOS circuitry 30 on posterior surface of second die 15, enabled by the presence of through-substrate vias 1. FIG. 1B illustrates a first die stack 10 with CMOS circuitry 30 on an anterior surface of a second die 15 and a third die 20, enabled by the presence of through-substrate vias 1 on the second die 15. FIG. 1C illustrates a first die stack 10, mounted on a printed circuit board ("PCB") 35 containing assorted electrical circuit components, with CMOS circuitry 30 on an anterior surface of a second die 15, enabled by the presence of through-substrate vias 1 on the second die 15. FIG. 1D illustrates a first die stack 10, mounted on a PCB 35 containing assorted electrical circuit components, with CMOS circuitry 30 on anterior surface of a second die 15, enabled by the presence of wire bonds 50 on the second die 15. FIG. 1E illustrates a die stack, mounted on a PCB 35 which comprises electrical circuit components 37 such as a potentiostat, an analog front end, an amplifier, a filter, an analog-to-digital converter, microcontroller, and a wireless radio, with CMOS circuitry 30 on a posterior surface of the second die 15, enabled by the presence of through-substrate vias 1 on both the second die 15 and PCB 35, and through anterior conductive pads 36 on the PCB 35, which are connected to posterior conductive pads 16 of the second die 15. A TSV 40 through the PCB 35 enables the connection to the electrical components 37 located on the posterior surface of the PCB 35.

Figure 2:
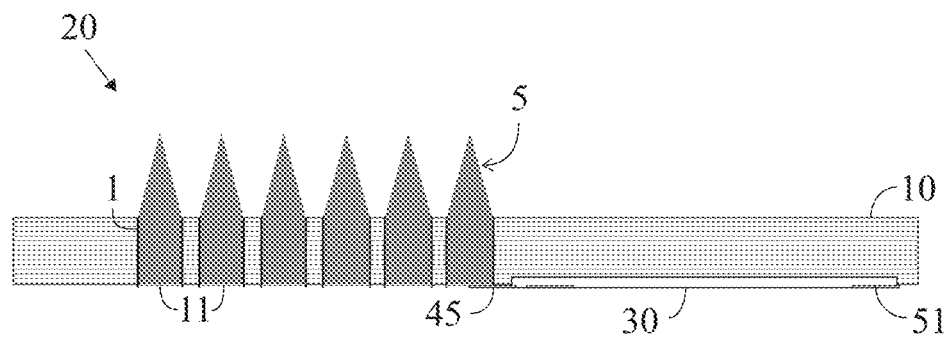
FIG. 2 illustrates microneedles on an anterior surface of die and CMOS circuitry on posterior surface of the die.
Figure 2A:
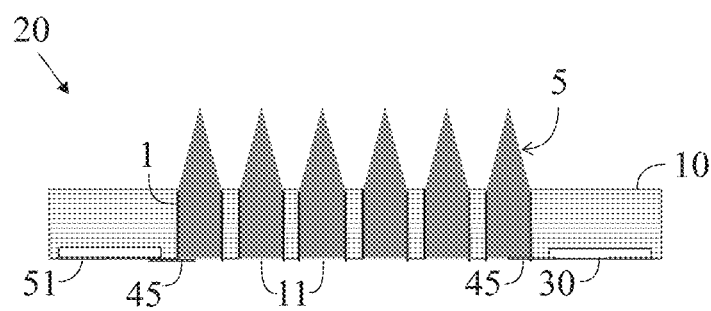
FIG. 2A illustrates microneedles on an anterior surface of die and CMOS circuitry on posterior surface of the die.
Figure 2B:
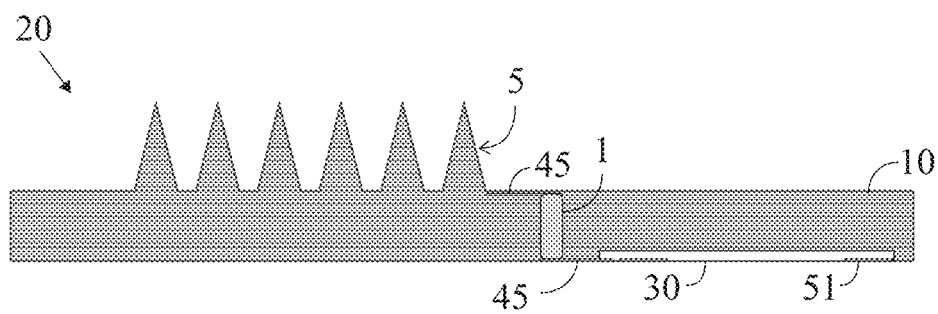
FIG. 2B illustrates microneedles on an anterior surface of die and CMOS circuitry on posterior surface of said die.
Figure 2C:
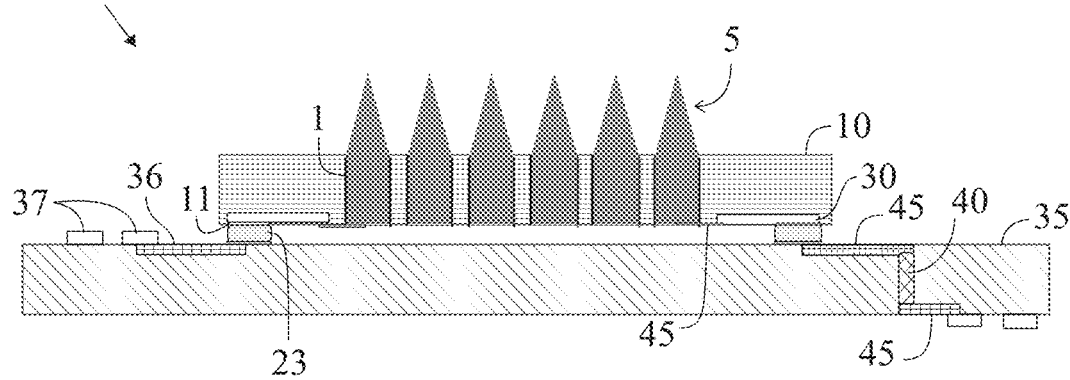
FIG. 2C illustrates microneedles on an anterior surface of die and CMOS circuitry on posterior surface of said die.

FIGS. 2-2C illustrate diagrammatic representations of various co-substrate devices 20 that achieve heterogeneous integration of silicon-fabricated solid microneedle sensors and CMOS circuitry. As shown in FIGS. 2 and 2A, microneedles 5 are positioned on an anterior surface of die 10 with CMOS circuitry 30 on a posterior surface of the die 10, and an interconnect between the microneedles 5 and the CMOS circuitry 30 is enabled by the presence of through-substrate vias 1 positioned collinearly with the microneedles 5 and a conductive trace 45. A bonding pad 51 is positioned on the CMOS circuitry 30. Posterior pads 11 are positioned below the microneedles 5. As shown in FIG. 2B, microneedles 5 are positioned on an anterior surface of a die 10 with CMOS circuitry 30 on a posterior surface of the die 10, and an interconnect is enabled by the presence of through-substrate vias 1 positioned in a spatially distinct region from the microneedles 5. As shown in FIG. 2C, the microneedles 5 are positioned on an anterior surface of a die 10 with CMOS circuitry 30 on a posterior surface of the die 10, and an interconnect is enabled by the presence of through-substrate vias 1 positioned collinearly with the microneedles 5, and the die 10 is mounted on a PCB 35 which comprises electrical circuit components 37 such as a potentiostat, an analog front end, an amplifier, a filter, an analog-to-digital converter, microcontroller, and a wireless radio, with an electrical interconnect achieved between the die 10 and the PCB 35 by means of stud bumps 23, solder balls 23, and/or conductive epoxy 23, and with an anterior conductive pad 36. A TSV 40 connects traces 45 on the anterior surface and posterior surface of the PCB 35.

Figure 3:
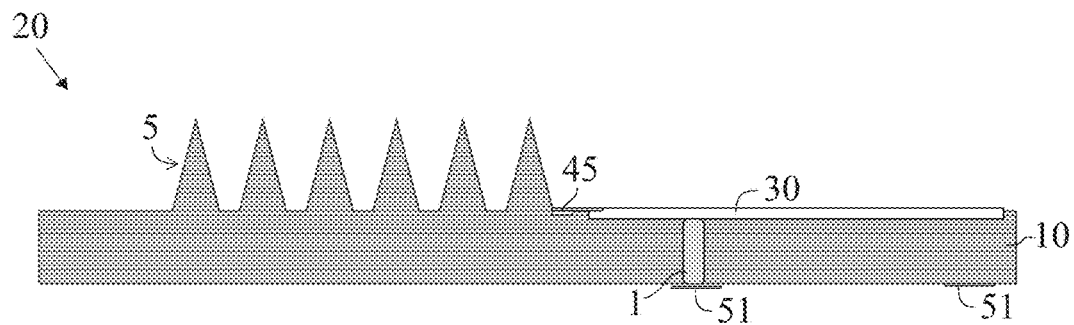
FIG. 3 illustrates microneedles and CMOS circuitry co-located on an anterior surface of die in spatially distinct regions.
Figure 3A:
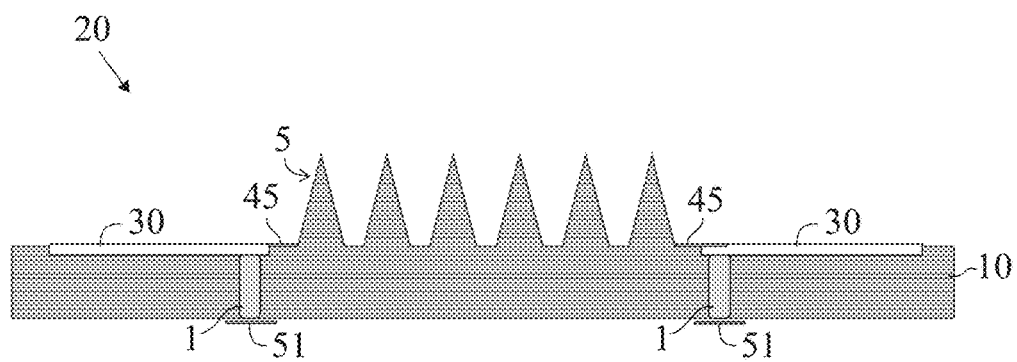
FIG. 3A illustrates microneedles and CMOS circuitry co-located on an anterior surface of die in spatially distinct regions.
Figure 3B:
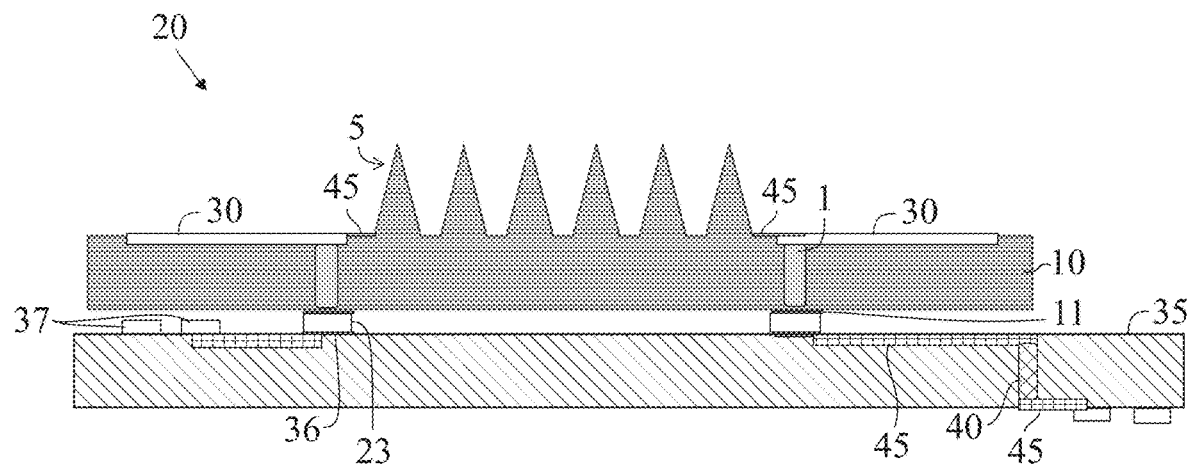
FIG. 3B illustrates microneedles and CMOS circuitry co-located on an anterior surface of die in spatially distinct regions.

FIGS. 3-3B illustrate diagrammatic representations of various co-planar devices 20 that achieve heterogeneous integration of silicon-fabricated solid microneedle sensors and CMOS circuitry. As shown in FIGS. 3 and 3A, microneedles 5 and CMOS circuitry 30 are co-located on an anterior surface of a die 10 in spatially distinct regions, and interconnects between the microneedles 5 and the CMOS circuitry 30 are enabled by the presence of conductive traces 45 positioned co-planarly with the CMOS circuitry 30. Anterior bonding pads 51 are on an anterior surface of the die 10. A TSV 1 connects the CMOS circuitry 30 to the anterior bonding pad 51. As shown in FIG. 3B, microneedles 5 and CMOS circuitry 30 are co-located on an anterior surface of a die 10 in spatially distinct regions, and interconnects between the microneedles 5 and the CMOS circuitry 30 are enabled by the presence of conductive traces 45 positioned co-planarly with the CMOS circuitry 30. The die 10 is mounted on a PCB 35 which comprises electrical circuit components 37 such as a potentiostat, an analog front end, an amplifier, a filter, an analog-to-digital converter, microcontroller, and a wireless radio. An electrical interconnect is achieved between the die 10 and the PCB 35 by means of through-substrate vias 1 in conjunction with stud bumps 23, solder balls 23, and/or conductive epoxy 23, and with an anterior conductive pad 36. A TSV 40 connects traces 45 on the anterior surface and posterior surface of the PCB 35.

One embodiment is a skin-adorned physiological or biochemical sensing device 20. The device 20 comprises a first substrate 10 and a second substrate 15. The first substrate 10 comprises an anterior surface and a posterior surface. The first substrate 10 comprises an array of solid microneedles 5 on the anterior surface designed to penetrate a biological interface to access a physiological fluid or tissue. Each microneedle 5 contains an addressable metal electrode located on the surface of the microneedle 5 which is in electrical communication with a metal surface located on the posterior surface of the first substrate 10 by means of a conductive conduit 1, to form a microneedle sensor component 5 capable of electrical interface with the physiological fluid or tissue. The conductive conduit 1 preferably comprises at least one of a through-substrate via 1. The through-substrate via 1 is preferably comprised of a doped or intrinsically conducting semiconductor; said semiconductor includes at least one of silicon, germanium, silicon germanium, gallium arsenide, indium phosphide, gallium nitride, zinc oxide, and cadmium selenide. The second substrate 15 has an anterior and a posterior surface. The second substrate 15 comprises integrated circuitry 30 on the anterior surface designed to transduce at least one signal produced by an electrophysiological or electrochemical reaction occurring at the metal electrode, to form a transducer component. The posterior surface of the first substrate 10 is stacked to the anterior surface of the second substrate 15. The first substrate 10 is bonded to the second substrate 15 to create an electrical interconnect between the first substrate 10 and the second substrate 15. A sensing device 20 is formed that is capable of interpreting the signal arising from the electrophysiological or electrochemical reaction to ascertain the level of some physiological or biochemical entity.

The first substrate is preferably a semiconductor that includes at least one of silicon, germanium, silicon germanium, gallium arsenide, indium phosphide, gallium nitride, zinc oxide, and cadmium selenide.

The electrical interface preferably includes at least one of applying an electrical stimulus to said physiological fluid or tissue and detecting an electrical signal arising within said physiological fluid or tissue. The electrical stimulus includes at least one of a DC voltage, DC current, AC voltage, AC current, frequency-modulated signal, amplitude-modulated signal, or phase-modulated signal. The electrical signal includes at least one of a DC voltage, DC current, AC voltage, AC current, frequency-modulated signal, amplitude-modulated signal, or phase-modulated signal.

The integrated circuitry 30 preferably comprises at least one of a potentiostat, an analog front end, an amplifier, a filter, an analog-to-digital converter, microcontroller, and a wireless radio.

The bonding means is at least one of stud bumps, solder balls, direct bonding, surface activated bonding, plasma activated bonding, fusion bonding, metal layer bonding, anodic bonding, eutectic bonding, glass frit bonding, insulating layer bonding, adhesive bonding, thermocompression bonding, reactive bonding, transient liquid phase diffusion bonding, physical bonding, and chemical bonding.

The second substrate 15 is further attached to a PCB 35 by means of at least one of: wire bonds 50, stud bumps 23, and solder balls 23.

The PCB 35 preferably comprises discrete electrical or electronic devices such as, but not limited to, batteries, antennas, resistors, capacitors, inductors, diodes, transistors, and discrete semiconductor components.

McCanna et al., U.S. patent application Ser. No. 14/843,926, filed on Sep. 2, 2015, for a Miniaturized Sub-Nanoampere Sensitivity Low-Noise Potentiostat System is hereby incorporated by reference in its entirety.

Windmiller et al., U.S. patent application Ser. No. 14/955,850, filed on Dec. 1, 2015, for a Method And Apparatus For Determining Body Fluid Loss is hereby incorporated by reference in its entirety.

Windmiller, U.S. patent application Ser. No. 15/177,289, filed on Jun. 8, 2016, for a Methods And Apparatus For Interfacing A Microneedle-Based Electrochemical Biosensor With An External Wireless Readout Device is hereby incorporated by reference in its entirety.

Wang et al., U.S. Patent Publication Number 20140336487 for a Microneedle Arrays For Biosensing And Drug Delivery is hereby incorporated by reference in its entirety.

Windmiller, U.S. patent application Ser. No. 15/590,105 for a Tissue-Penetrating Electrochemical Sensor Featuring A Co Electrodeposited Thin Film Comprised Of A Polymer And Bio-Recognition Element is hereby incorporated by reference in its entirety.

Windmiller, et al., U.S. patent application Ser. No. 15/913,709, filed on Mar. 6, 2018, for Methods For Achieving An Isolated Electrical Interface Between An Anterior Surface Of A Microneedle Structure And A Posterior Surface Of A Support Structure is hereby incorporated by reference in its entirety.

PCT Application Number PCT/US17/55314 for an Electro Deposited Conducting Polymers For The Realization Of Solid-State Reference Electrodes For Use In Intracutaneous And Subcutaneous Analyte-selective Sensors is hereby incorporated by reference in its entirety.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention the following:

1. A skin-adorned physiological or biochemical sensing device, said device comprising:
    a first substrate comprising an anterior surface and a posterior surface;
    said first substrate comprising an array of solid microneedles on the anterior surface designed to penetrate a biological interface to access a physiological fluid or a tissue, each microneedle containing an addressable metal electrode located on the surface of said microneedle and in electrical communication through a corresponding first conductive conduit with a metal surface located on the posterior surface, each first conductive conduit extending through the entire first substrate, wherein said anterior surface of said first substrate is configured to act as an electrical interface with said physiological fluid or said tissue, wherein each first conductive conduit comprises a through-substrate via and a conductive trace;
    a second substrate comprising an anterior surface and a posterior surface;
    said second substrate comprising integrated circuitry on said anterior surface designed to transduce at least one signal produced by an electrophysiological or electrochemical reaction occurring at said metal electrode, wherein each first conductive conduit of said first substrate corresponds to a second conductive conduit of the second substrate, each second conductive conduit extending through the entire second substrate to contact the integrated circuitry, each first conductive conduit comprises a through-substrate via and a conductive trace, wherein said anterior surface of said second substrate is configured to act as a transducer component, wherein said integrated circuitry comprises a potentiostat or a galvanostat;
    wherein the posterior surface of the first substrate is stacked to the anterior surface of the second substrate;
    wherein the first substrate is bonded to the second substrate, to form an electrical interconnect between the said first substrate and the second substrate; and
    wherein the sensing device is configured to interpret said at least one signal from said electrophysiological or electrochemical reaction to ascertain the level of a physiological or biochemical entity.

2. The device of claim 1, wherein said second substrate is a semiconductor.

3. The device of claim 2, wherein said semiconductor includes at least one of silicon, germanium, silicon germanium, gallium arsenide, indium phosphide, gallium nitride, zinc oxide, and cadmium selenide.

4. The device of claim 1, wherein said electrical interface is configured to apply an electrical stimulus to said physiological fluid or said tissue and configured to detect an electrical signal arising within said physiological fluid or said tissue.

5. The device of claim 4, wherein said electrical stimulus includes at least one of a DC voltage, DC current, AC voltage, AC current, frequency-modulated signal, amplitude-modulated signal, or phase-modulated signal.

6. The device of claim 4, wherein said electrical signal includes at least one of a DC voltage, DC current, AC voltage, AC current, frequency-modulated signal, amplitude-modulated signal, or phase-modulated signal.

7. The device of claim 1, wherein said integrated circuitry further comprises at least one of an analog front end, an amplifier, a filter, an analog-to-digital converter, microcontroller, or a wireless radio.

8. The device of claim 1, wherein said integrated circuitry is comprised of complementary metal oxide semiconductor constituents.

9. The device of claim 1, wherein said through-substrate via is comprised of a doped or intrinsically conducting semiconductor; said semiconductor includes at least one of silicon, germanium, silicon germanium, gallium arsenide, indium phosphide, gallium nitride, zinc oxide, and cadmium selenide.

10. The device according to claim 1, wherein said bonding means at least one of: stud bumps, solder balls, direct bonding, surface activated bonding, plasma activated bonding, fusion bonding, metal layer bonding, anodic bonding, eutectic bonding, glass frit bonding, insulating layer bonding, adhesive bonding, thermocompression bonding, reactive bonding, transient liquid phase diffusion bonding, physical bonding, and chemical bonding.

11. The device according to claim 1, wherein said second substrate is further attached to a printed circuit board by means of at least one of: wire bonds, stud bumps, and solder balls.

12. The device according to claim 11, wherein said printed circuit board contains discrete electrical or electronic devices such as, but not limited to, batteries, antennas, resistors, capacitors, inductors, diodes, transistors, and discrete semiconductor components.

13. A skin-adorned physiological or biochemical sensing system, said device comprising:
a substrate comprising an anterior surface and a posterior surface;
said anterior surface comprising an array of solid microneedles designed to penetrate a biological interface to access a physiological fluid or tissue, each microneedle containing an addressable metal electrode located on the surface of said microneedle and in electrical communication through a corresponding first conductive conduit with a metal surface located on the posterior surface of the substrate, each first conductive conduit extending through the entire substrate, wherein said anterior surface of said substrate is configured to act as an electrical interface with said physiological fluid or said tissue, wherein each first conductive conduit comprises a through-substrate via and a conductive trace;
said posterior surface comprising integrated circuitry located adjacent to said through-substrate via and designed to transduce an at least one signal produced by an electrophysiological or electrochemical reaction occurring at said metal electrode, said metal electrode in electrical communication with the integrated circuitry through each first conductive conduit, wherein said posterior surface of said substrate is configured to act as a transducer component, wherein said integrated circuitry comprises a potentiostat or a galvanostat; and
wherein the sensing device is configured to interpret said at least one signal from said electrophysiological or electrochemical reaction to ascertain the level of a physiological or biochemical entity.

14. The device of claim 13, wherein said substrate is a semiconductor.

15. The device of claim 13, wherein said semiconductor includes at least one of silicon, germanium, silicon germanium, gallium arsenide, indium phosphide, gallium nitride, zinc oxide, and cadmium selenide.

16. The device of claim 13, wherein said electrical interface is configured to apply an electrical stimulus to said physiological fluid or said tissue and configured to detect an electrical signal arising within said physiological fluid or said tissue.

17. The device of claim 16, wherein said electrical stimulus includes at least one of a DC voltage, DC current, AC voltage, AC current, frequency-modulated signal, amplitude-modulated signal, or phase-modulated signal.

18. The device of claim 16, wherein said electrical signal includes at least one of a DC voltage, DC current, AC voltage, AC current, frequency-modulated signal, amplitude-modulated signal, or phase-modulated signal.

19. A skin-adorned physiological or biochemical sensing device, said device comprising:
a first substrate comprising an anterior surface and a posterior surface;
a second substrate comprising an anterior surface and a posterior surface;
a printed circuit board;
wherein said first substrate comprising an array of solid microneedles on the anterior surface designed to penetrate a biological interface to access a physiological fluid or a tissue, each microneedle containing an addressable metal electrode located on the surface of said microneedle and in electrical communication through a corresponding first conductive conduit with a metal surface located on the posterior surface, each first conductive conduit extending through the entire first substrate, wherein said anterior surface of said first substrate is configured to act as an electrical interface with said physiological fluid or said tissue, wherein each first conductive conduit comprises a through-substrate via and a conductive trace;
wherein said second substrate comprising CMOS circuitry on said anterior surface designed to transduce at least one signal produced by an electrophysiological or electrochemical reaction occurring at said metal electrode, wherein each first conductive conduit of said first substrate corresponds to a second conductive conduit of the second substrate, each second conductive conduit extending through the entire second substrate to contact the integrated circuitry, each first conductive conduit comprises a through-substrate via and a conductive trace, wherein said anterior surface of said second substrate is configured to act as a transducer component, wherein said CMOS circuitry comprises a potentiostat or a galvanostat;
wherein the posterior surface of the first substrate is stacked to the anterior surface of the second substrate, and the posterior surface of the second substrate is bonded to the printed circuit board;
wherein the printed circuit board comprising a plurality of through-substrate vias;
wherein the first substrate is bonded to the second substrate, to form an electrical interconnect between the said first substrate and the second substrate; and
wherein the sensing device is configured to interpret said at least one signal from said electrophysiological or electrochemical reaction to ascertain the level of a physiological or biochemical entity.

* * * * *